United States Patent [19]

Lin et al.

[11] Patent Number: 4,533,756

[45] Date of Patent: Aug. 6, 1985

[54] PROCESS FOR SYNTHESIS OF ACRYLIC ACID PRECURSORS VIA HYDROFORMYLATION OF VINYL ETHER

[75] Inventors: Jiang-Jen Lin, Round Rock; Walter H. Brader, Jr., Austin, both of Tex.

[73] Assignee: Texaco Inc., White Plains, N.Y.

[21] Appl. No.: 548,909

[22] Filed: Nov. 7, 1983

[51] Int. Cl.$^3$ ............................................. C07C 45/50
[52] U.S. Cl. ................................. 568/454; 568/909
[58] Field of Search .......................... 568/454, 909

[56] References Cited

U.S. PATENT DOCUMENTS

| | | | |
|---|---|---|---|
| 3,917,661 | 11/1975 | Pruett et al. | 568/454 |
| 4,064,145 | 12/1977 | Taylor | 568/454 |
| 4,229,381 | 10/1980 | Ogata et al. | 568/454 |
| 4,262,142 | 4/1981 | Sherman et al. | 568/454 |
| 4,302,394 | 11/1981 | Dennis | 568/454 |
| 4,383,125 | 5/1983 | Harris et al. | 568/454 |
| 4,414,420 | 11/1983 | Harris et al. | 568/454 |

*Primary Examiner*—Werren B. Lone
*Attorney, Agent, or Firm*—Jack H. Park; Kenneth R. Priem; Cynthia L. Kendrick

[57] ABSTRACT

A process is disclosed for the preparation of acrylic acid precursors by a hydroformylation process which comprises reacting a vinyl ether with carbon monoxide and hydrogen in the presence of a catalyst comprising a rhodium carbonyl compound and a phosphine ligand at a mild temperature and pressure until there is substantial formation of the intermediate 2- and 3-ethoxypropanals, followed by oxidation of said aldehydes and pyrolysis to said acrylic acid.

12 Claims, No Drawings

PROCESS FOR SYNTHESIS OF ACRYLIC ACID PRECURSORS VIA HYDROFORMYLATION OF VINYL ETHER

FIELD OF THE INVENTION

This invention concerns an improved process for hydroformylation of vinyl ether to produce intermediate products for acrylic acid synthesis.

BACKGROUND OF THE INVENTION

Hydroformylation reactions wherein olefinic substrates are reacted with carbon monoxide and hydrogen to form an aldehyde are known in the art and provide important building blocks for the petrochemical industry.

One of the early processes for producing acrylic acid was the Reppe reaction, which involves the reaction of acetylene with carbon monoxide using a nickel carbonyl catalyst and high pressure. Two inherent disadvantages of using acetylene are high cost and explosion danger.

Other routes included producing beta-propiolactone, starting from ketene, and alcoholysis of acrylonitrile.

Ohara, et al, in "Oxidize Propylene to Acrylics" Hydrocarbon Processing, p. 85–88 (Nov., 1972) discuss the Nipon Shokubai process wherein propylene is oxidized to acrylic acid and esterfied to key acrylic esters. The polyvalent metal oxide catalyst for this reaction, containing predominantly molybdenum was not highly satisfactory with respect to selectivity to acrylic acid and catalyst life. When tellurium oxide was used as a promoter in an attempt to increase selectivity to acrylic acid, it was found the oxide was gradually reduced to tellurium metal.

Another disadvantage of using the process starting with propylene to produce acrylic acid is that acrylic acid has a tendency to polymerize and acrylic acid produced by propylene oxidation tends to have a higher polymerization rate in the recovery and purification steps compared to acrylic acid made by other processes and therefore, polymerization prevention steps have to be incorporated.

In "A New Route to Acrylic Acid", Hydrocarbon Processing p. 95–96 (November 1972), Olivier, et al. disclose a new route to acrylic acid which uses ethylene in place of acetylene. Under anhydrous conditions ethylene reacts with carbon monoxide and oxygen in a titanium-clad reactor with a palladium-copper catalyst, in acetic acid solution to form a mixture of acrylic acid and β-acetoxypropionic acid. In this process the reaction medium must constantly be kept anhydrous and requires the use of a drying agent which is most commonly acetic anhydride.

In the practice of this process, the concentration of anhydride has a marked effect on both reaction rate and relative selectivity to acrylic acid. In addition it is necessary to carry out the reaction in a high boiling point acid to facilitate recovery of acrylic acid. However, if the high boiling point acid is used as the only solvent, it can reduce the rate of the reaction.

In an article on hydroformylation by R. L. Pruett in *Adv. Organometallic Chem.*, 17, p. 1 (1979) there is a discussion of the background of hydroformylation reactions, including commercial utilization, substrates, catalysts, products and reaction mechanisms.

G Krsek and H. Adkins reported in J. Am. Chem. Soc. 71, 3051 (1949) that n-butyl vinyl ether was hydroformylated by the use of cobalt carbonyl catalyst, which gave low yields of products (~31%) with the formyl groups exclusively in the α position.

Acrylic vinyl ethers, such as dihydropyran and its derivatives, were hydroformylated with a cobalt catalyst at high temperature and pressure (180 psi and 300 atm of $CO/H_2$ 1:2), in a process reported by Falbe and Korte, Chem. Ber. 97, 1104 (1964).

In U.S. Pat. No. 2,497,303, W. F. Gresham et al. disclosed the cobalt hydroformylation of methyl vinyl ether at the conditions of 160°–175° C. and 645~720 atm to give 3-methoxypropionaldehyde.

A review article, "Synthesis of Intermediates by Rhodium-Catalyzed Hydroformylation" of Angew. Chem. Int. Ed. Engl. 19, 178–183 (1980) by H. Siegel and W. Himmele reported the hydroformylation of 2-aryloxypropanal synthesis from aryl vinyl. Similar results were also reported by J. M. Brown, Chemistry and Industry (Oct. 2 1982) pp. 737.

The use of carbonylhydridotris(triphenylphosphine)rhodium(I) for hydroformylation of various olefinic substrates and its mechanism was reviewed by F. H. Jardine, Polyhedron Vol. 1, No. 7–8, pp. 569–605 (1982).

The importance of the use of various phosphine ligands in combination with a rhodium hydroformylation catalyst for functionalized olefins, such as vinyl acetate, allyl acetate, 3-butenyl acetate, ethyl acrylate, allyl alcohol, allyl butyl ether and 3-butenyl butyl ether, has been examined. But the reaction of vinyl ether using a rhodium catalyst has still remained unreported.

U.S. Pat. No. 4,072,709, issued to Monsanto Company discloses a hydroformylation/oxidation process to produce alphaacetoxy-propionaldehyde from vinyl ester. The hydroformylation of vinyl ester has also been reported by J. Mol. Cat. 18 (1983), 381–390, J. Mol. Cat. 2 (1977) 301–306, DT 2504-981 and Fr. Demande FR 2,477,140.

Another discussion of hydroformylation is presented in "Hydroformylation, Oxo Synthesis, Roelen Reaction" by J. Falbe, *New Synthesis with Carbon Monoxide*, (1980).

It would be a considerable advance in the art to devise a novel method for synthesis of acrylic acid intermediate products which demonstrates improved conversion and yields, employs a catalyst with increased activity and uses mild reaction conditions.

SUMMARY OF THE INVENTION

These and other desirable results are achieved by the process of this invention comprising preparing acrylic acid by a hydroformylation process which comprises reacting a vinyl ether with a carbon monoxide and hydrogen in the presence of a catalyst comprising a rhodium-containing compound and a triphosphine ligand at a temperature of 50°–150° C. and a pressure of from about 100 psi to 1000 psi until there is substantial formation of the intermediate 2- and 3-ethoxypropanal followed by oxidation of said aldehydes and pyrolysis to said acrylic acid.

DETAILED DESCRIPTION OF THE INVENTION

In the narrower and more preferred practice of this invention, acrylic acid precursors, such as 2- and 3-ethoxypropanals are prepared from a synthesis gas mixture of carbon monoxide, hydrogen and vinyl ether by a process comprising the following steps:

(a) Contacting said mixture of carbon monoxide, hydrogen and vinyl ether with a catalyst system comprising a rhodium-containing compound and a phosphine ligand, (b) Heating said reaction mixture to a temperature of 50°–150° C. and a pressure of from about 100 psi to 1000 psi and (c) Oxidizing said 2- and 3-ethoxypropanals contained therein and pyrolizing said compounds to produce acrylic acid.

In order to present the inventive concept in the greatest possible detail to promote its understanding, the following supplementary disclosure is submitted. The basic invention, improved upon here, is practiced as follows:

Catalysts which are suitable in the practice of this invention contain rhodium. The rhodium-containing catalyst may be chosen from a wide variety of organic or inorganic compounds, complexes, etc. It is only necessary that the catalyst precursor actually employed contain said metal in any of its ionic states. The actual catalytically active species is then believed to comprise rhodium in complex combination with carbon monoxide, hydrogen and phosphine ligands, ligands and optionally cobalt. The most effective catalyst is believed to be achieved where rhodium carbonyls are mixed with triphenylphosphine ligands under reaction conditions.

The rhodium catalyst precursors may take many different forms. For instance, the rhodium may be added to the reaction mixture in a carbonyl form, as in the case of, for example, rhodium carbonyl hydrate, hexarhodium hexadecacarbonyl $Rh_6(CO)_{16}$ and hydridocarbonyltris(triphenylphosphine) rhodium(I), $HRh(CO)(PPh_3)_3$.

Preferred rhodium-containing compounds are carbonyls of rhodium. Among the particularly preferred is hydridocarbonyltris(triphenylphosphine) rhodium(I) $Rh(CO)(PPh_3)_3$. The usefulness of these rhodium compounds for aldehyde synthesis is illustrated by the accompanying Examples.

The rhodium-containing compound is used in conjunction with a phosphonium ligand. Examples include triphenyl phosphine, tri-n-butylphosphine and 1,1'-bis(-diphenylphosphine ferrocene. Triphenylphosphine is preferred.

The substrates employed in the practice of this invention include ethers containing two to six carbon atoms and mixtures of the same. Examples of suitable ethers include ethers such as vinyl ethyl ether, vinyl ether, vinyl methyl ether, vinyl n-butyl ether, vinyl sec-butyl ether and vinyl phenyl ether.

Particularly preferred are ethers such as ethyl vinyl ether.

A solvent or liquid diluent is not necessary in the process of this invention, although one may be used. A wide variety of solvents or diluents may be used, including hydrocarbon and oxygenated hydrocarbons. Suitable oxygenated hydrocarbon solvents are compounds composed only of carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms.

The solvent can also be an aromatic or aliphatic amide. The amide solvent can be selected from the group consisting of N-methylpyrolidone and N,N-dimethylformamide.

Preferred ester type solvents are the aliphatic and acyclic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents are, for example, cyclic ketones including cyclohexanone, 2-methylcyclohexanone, as well as acylic ketones including 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include N-butyl vinyl ether, vinyl phenyl ether, ethyl vinyl ether, isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers, including 1,4-dioxane or p-dioxane, etc. Hydrocarbon solvents, such as hexane, heptane, decane, dodecane, tetradecane, etc. are also suitable solvents for use in this invention. Toluene may also be used.

In the practice of this invention, it is also possible to add a small amount of water to the solvent or diluent and still obtain satisfactory results.

The quantity of rhodium catalyst employed in the instant invention is not critical and may vary over a wide range. In general, the novel process is desirably conducted in the presence of a catalytically effective quantity of the active rhodium species and phosphine ligand which gives the desired products in reasonable yields. The reaction proceeds when employing as little as about $1 \times 10^{-6}$ weight percent, and even lesser amounts, of rhodium together with about one weight percent of phosphine ligand, basis the total weight of the reaction mixture. The upper concentration is dictated by a variety of factors including catalyst cost, partial pressures of carbon monoxide and hydrogen, operating temperature etc. A rhodium catalyst concentration of from about $1 \times 10^{-5}$ to about 1 weight percent rhodium in conjunction with a phosphine ligand concentration of from about $1 \times 10^{-3}$ to about $1 \times 10$ weight percent, based on the total weight of reaction mixture is generally desirable in the practice of this invention. The preferred rhodium phosphine ligand atomic ratio is about 3 to 100.

The temperature range which can usefully be employed in these syntheses is a variable dependent upon other experimental factors, including the pressure, the concentration and the choice of the particular species of rhodium catalyst among other things. The range of operability is from about 50° to 150° C. when superatmospheric pressures of syngas are employed. A narrow range of 90°–150° C. represents the preferred temperature range.

Superatmospheric pressures of 100 psi or greater lead to substantial yields of aldehydes by the process of this invention. A preferred operating range is above 500 psi. The most preferred range is from 600–800 psi, but pressures of as much as 1000 psi or more can be used.

The relative amounts of carbon monoxide and hydrogen which may be initially present in the syngas mixture are variable, and these amounts may be varied over a wide range. In general, the mole ratio of CO—to—$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases of the group including nitrogen, argon, neon and the like, or they may include gases that may or may not undergo reaction under CO hydrogenation conditions, as represented by carbon dioxide and hydrocarbons including methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The novel process of this invention can be conducted in a batch, semi-continuous or continuous fashion and said material may be recovered by methods well known in the art, such as distillation, fractionation, extraction and the like.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. All temperatures are in degrees centigrade and all pressures are in pounds per square inch gauge (psig).

Having described the inventive process, the following examples are submitted to supply specific and illustrative embodiments.

EXAMPLE I (5631-78A)

In this example a 300 ml stainless steel magnedrive reactor was charged with hydridocarbonyltris (triphenylphosphine)rhodium (I) HRh(CO) (PPh$_3$)$_3$ (0.046 g, 0.05 mmole), Ph$_3$P (1.3 g), ethyl vinyl ether (10.0 g) and p-dioxane (10.0 g). The system was purged of air with CO/$H_2$ mixture, pressured to 100 psi with CO/$H_2$ mixtures (molar ratio 1:2) and then heated to 130° C. At this temperature the pressure was raised to 800 psi with CO/$H_2$ (1:2). During the reaction process, the CO/$H_2$ was consumed and the pressure of 800 psi was maintained by additional supply of synthesis gas. After the designated reaction time (1.5 hr.) the reactor was allowed to cool down to room temperature. The excess gas was vented off and the product liquid was recovered. The liquid sample (brown solution) was analyzed by glc and calculated to be:

ethyl vinyl ether conversion 100%
Product selectivities:
2-ethoxypropanal: 43%,
3-ethoxypropanal: 50%,
diethyl ether: 7%.

EXAMPLE II

Example II was conducted by the same procedure as Example I. In this example hexarhodium hexadecacarbonyl, Rh$_6$(CO)$_{16}$ (0.0090 g. 0.050 mm) was the rhodium compound used and the ligand used was 1,1'-bis(diphenylphosphine)ferrocene (0.28 g). Toluene (15 g) was used as a solvent and 5.0 g ethyl vinyl ether was used.

Reaction time period was 4 hours.

When the liquid product was recovered and analyzed by glc the product selectivities were found to be:

Ethyl vinyl conversion: 80%
Product selectivities:
2-ethoxypropanal: 30%,
3-ethoxypropanal: 70%,
diethyl ether: -.

EXAMPLES III-VII

Examples III-VII were conducted by the same procedure as used in Example I. It is noted that a larger weight percent of rhodium-containing compound is used in Example V and no phosphine ligand or solvent is used. In Example VI, the solvent used is dimethylformamide, whereas Examples III, IV and VII use p-dioxane.

It is also noted that the ether used as a substrate in Example VII is a n-butyl vinyl ether. Results are shown in Table I.

TABLE I

| | HYDROFORMYLATION OF ETHYL VINYL ETHER AND n-BUTYL VINYL ETHER | | | | | | | | | |
|---|---|---|---|---|---|---|---|---|---|---|
| Example | Catalyst | Ligand | Solvent | Ethyl vinyl ether (used) | Reaction Conditions | S. M. Conversion | 2-alkoxy-propanal | 3-alkoxy-propanal | diethyl ether | Productivity |
| III | HRh(CO) (PPh$_3$)$_3$ (0.046 g, 0.050 mm) | Ph$_3$P (1.3 g) | p-dioxane (10.0 g) | (10.0 g) | CO/$H_2$ = 1:2 800 psi ca.130° C., 1.5 hr | 100% | 43% | 50% | 7% | 133,000 g/g-atm-Rh/hr or 0.31 g/cc/hr |
| | HRh(CO) (PPh$_3$)$_3$ (0.046 g, 0.050 mm) | Ph$_3$P (1.3 g) | p-dioxane (10.0 g) | " | CO/$H_2$ = 1:2 800 psi ca.130° C., 1.5 hr | 100% | 40% | 53% | 6% | |
| V | HRh(CO) (PPh$_3$)$_3$ (0.092 g, 0.1 mmole) | None | None | (20.0 g) | CO/$H_2$ = 1:2 800 psi ca.130° C., 1 hr. | 69% | 62% | 38% | ~0% | 138,000 g/g-atm-Rh/hr or 0.67 g/cc/hr |
| VI | HRh(CO) (PPh$_3$)$_3$ (0.046 g, 0.050 mm) | Ph$_3$P (1.3 g) | DMF (10.0 g) | (10.0 g) | CO/$H_2$ = 1:2 800 psi 123° C., 1 hr. | 65% | 38% | 42% | — | |
| VII | HRh(CO) (PPh$_3$)$_3$ (0.046 g, 0.050 mm) | Ph$_3$P (1.3 g) | p-dioxane (10.0 g) | n-butyl vinyl ether (10.0 g) | CO/$H_2$ = 1:2 800 psi, 122° C., 2 hrs. | 72% | 40% | 39% | — | |

What is claimed is:

1. A process for preparing acrylic acid precursors which comprises the steps of contacting a vinyl ether selected from the group consisting of n-butyl vinyl ether, vinyl phenyl ether, ethyl vinyl ether, vinyl ether, vinyl methyl ether, and vinyl sec-butyl, ether, carbon monoxide and hydrogen with a catalyst system comprising a rhodium-carbonyl compound and a phosphine ligand selected from the group consisting of triphenylphosphine, tri-n-butylphosphine and 1,1'-bis(diphenylphosphine)ferrocene, heating resultant reaction mixture under a pressure of 100 psi to 1000 psi at a temperature of 50° C. to about 150° C. and isolating said precursors of the group including 2- and 3-ethoxypropanal.

2. The process of claim 1 further comprising the addition of an oxygenated solvent to the reaction mixture.

3. The process of claim 2 wherein the solvent is a monocyclic or heterocyclic ether of the group including 1,4 dioxane.

4. The process of claim 1 further comprising the addition of an aromatic or aliphatic amide solvent.

5. The process of claim 4 wherein the amide solvent is selected from the group consisting of N-methyl pyrolidone and N,N dimethylformamide.

6. The process of claim 1 further comprising the addition of toluene as a solvent.

7. The process of claim 1 wherein the rhodium carbonyls are selected from the group consisting of
rhodium carbonyl hydrate,
hydrido-tris-(triphenylphosphino) carbonyl rhodium(I),
tetrarhodium dodecacarbonyl, and hexadecarhodium hexdecacarbonyl.

8. The process of claim 1 wherein the phosphonium ligand is triphenylphosphine.

9. The process of claim 1 wherein the phosphonium ligand is
1,1'-bis(diphenylphosphine)ferrocene.

10. The process of claim 1 wherein the mixture is under a pressure of 500–1000 psi.

11. The process of claim 1 wherein the temperature is 50°–150° C.

12. The process of claim 1 wherein the ether is ethyl vinyl ether.

* * * * *